United States Patent [19]

Smith et al.

[11] Patent Number: 4,804,367
[45] Date of Patent: Feb. 14, 1989

[54] SUSPENDABLE, THERMALLY INSULATING JACKET FOR I.V. FLUID BAGS

[76] Inventors: Robert K. Smith, Rte. 2, Box 147, Astoria, Oreg. 97103; Alan C. Pochert, 3926 N.E. 32nd Ave., Portland, Oreg. 97212

[21] Appl. No.: 34,635

[22] Filed: Apr. 6, 1987

[51] Int. Cl.⁴ .............................................. A61F 7/12
[52] U.S. Cl. ................................... 604/113; 604/408
[58] Field of Search ............... 604/408, 403, 399, 404, 604/141, 174, 113, 262; 128/DIG. 12, 399–402

[56] References Cited

U.S. PATENT DOCUMENTS

| 243,715 | 3/1977 | Trimnell | D83/1 R |
|---|---|---|---|
| 4,087,864 | 5/1978 | LaBove et al. | 604/174 |
| 4,090,514 | 5/1978 | Hinck et al. | 128/DIG. 12 |
| 4,096,897 | 6/1978 | Cammarata | 604/408 |
| 4,268,567 | 5/1981 | Harmony | 428/195 |
| 4,282,279 | 8/1981 | Strickland | 428/101 |
| 4,399,668 | 8/1983 | Williamson | 62/457 |
| 4,401,245 | 8/1983 | Zills | 224/148 |
| 4,424,190 | 1/1984 | Mather et al. | 604/408 |
| 4,462,444 | 7/1984 | Larson | 150/52 R |
| 4,551,136 | 11/1985 | Mandl | 604/141 |
| 4,581,011 | 4/1986 | Campbell | 604/29 |

FOREIGN PATENT DOCUMENTS 2515889  10/1976  Fed. Rep. of Germany ...... 604/113

Primary Examiner—John D. Yasko
Attorney, Agent, or Firm—Eugene D. Farley

[57] ABSTRACT

A suspendable, thermally insulating jacket for I.V. fluid bags. The jacket comprises a sheet of thermally insulating material enclosing the bag as it is applied in sick room use. A bag support hook and straps on the jacket support the I.V. bag within the sheet when the latter is in its bag-enclosing condition. A jacket support loop on the jacket support it on the I.V. pole or other support in the sick room. The jacket accordingly provides for maintaining the fluid contents of the I.V. bag at the desired temperature as they are administered to the patient.

2 Claims, 1 Drawing Sheet

U.S. Patent  Feb. 14, 1989  4,804,367
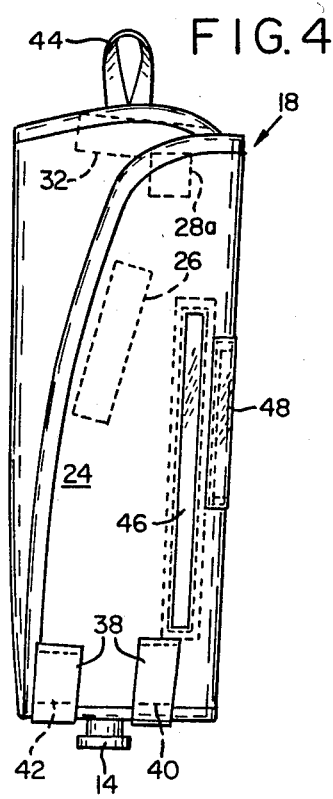
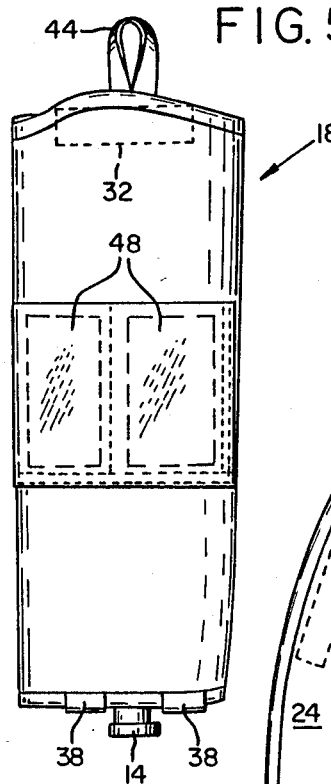
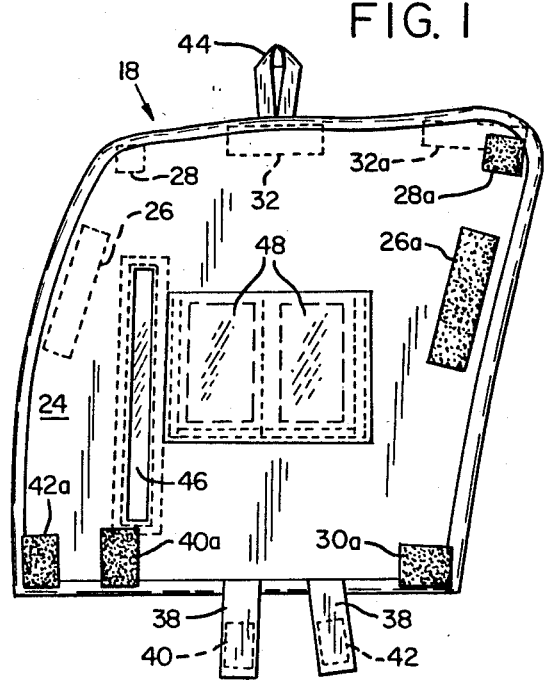
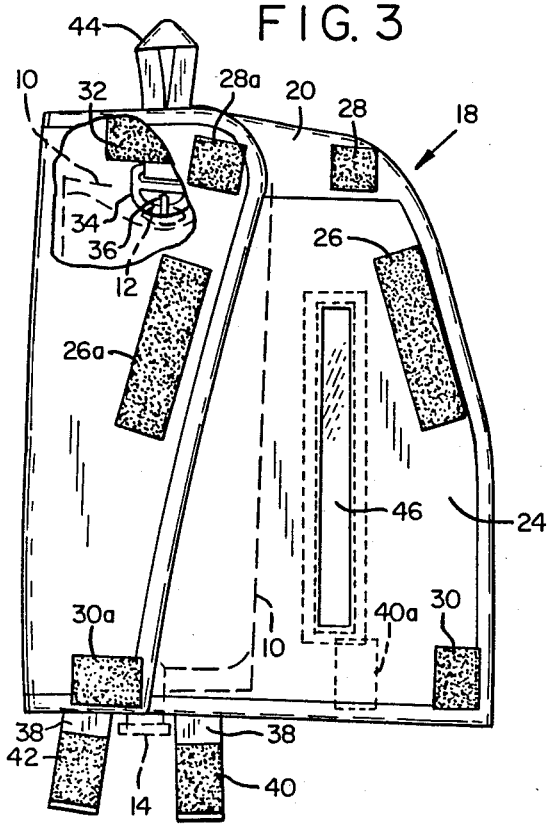
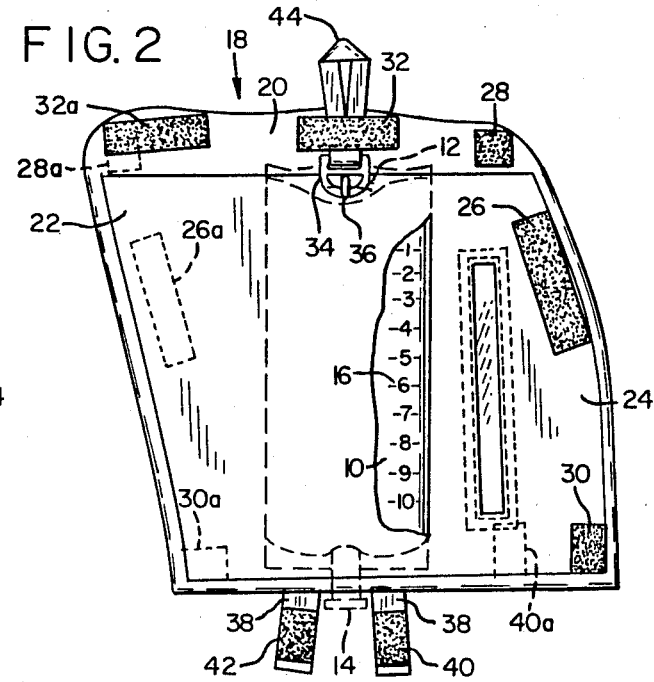

SUSPENDABLE, THERMALLY INSULATING JACKET FOR I.V. FLUID BAGS

BACKGROUND AND GENERAL STATEMENT OF THE INVENTION

This invention relates to the combination of an I.V. fluid bag (intravenous fluid bag) and a thermally insulating jacket therefor.

As a Certified Registered Nurse Anesthetist (CRNA) I, Robert K. Smith, one of the joint inventors herein, have been interested for several years in the challenge of keeping patients warm in surgery. By carefully monitoring patient temperatures, I have learned that when present operating room techniques are employed, it is not uncommon to see a 2° F. to 4° F. patient body temperature drop from the beginning of anesthetic administration to the time the patient enters the recovery room at the end of the surgery.

Several factors are responsible.

Prior to beginning a surgical procedure, an I.V. line usually is placed in one or more of the patient's veins. Fluid is rapidly infused through this line, in amounts varying from 400 ml. to 1500 ml. This fluid is normally at room temperature, some 28.6° F. less than the patient's normal temperature. This naturally has a pronounced cooling effect on the patient's body temperature.

This adverse effect is aggravated by the fact that, if general anesthesia is applied, the patient is rendered unable to regulate his body temperature.

Furthermore, in some procedures the patient is ventilated with gases which are piped into the operating room from outside the building. These gases are many degrees cooler than the body temperature of the patient. They frequently are administered by an endotracheal tube which bypasses the warming function of the nose.

Still another consideration is the fact that the patient's body is opened, allowing heat to escape. The bigger the opening, the more heat is lost.

It is very important to patient well-being and recovery that his body be maintained at its normal temperature. The patient is much more comfortable if such is the case. If the patient is cold, he will shiver. Shivering greatly increases oxygen consumption.

Furthermore, the patient will metabolize pre-, intra- and post-operatively drugs more rapidly. In sum, if his body temperature is normal he will be more comfortable and recover more rapidly.

Although in the usual situation the patient's body temperature will drop during an operation, there exists a hypermetabolic condition called Malignant Hyperthermia which sometimes occurs during anesthesia. In this condition the patient's temperature rises rapidly to very high levels, 106° to 108° F. or even higher. Part of the treatment of this condition is the rapid administration of cold I.V. fluids. One liter bags of normal saline are kept in the refrigerator of the operating room for this purpose. When these bags are removed from the refrigerator and hung in a room having a temperature of 70° F., they warm rapidly toward the ambient temperature, thus detracting from the efficiency of the treatment.

In both situations, i.e. that in which the patient's body temperature is lowered and that in which it is elevated it would be desirable to provide means for maintaining the temperature of the fluid contents of I.V. fluid bags at the optimum temperature level during the entire period of fluid administration, thereby minimizing, or avoiding entirely, conditions of hypothermia and hyperthermia.

It is the general purpose of the present invention to provide such a means.

Generally stated, the means by which this desired end result is accomplished is the provision, in combination with an I.V. fluid bag, of a thermally insulating jacket which comprises a sheet of thermally insulating material enclosing the bag. Bag support means on the jacket support the bag within the sheet in its bag-enclosing condition. Jacket support means on the jacket support it on an I.V. pole or other support. By preheating or precooling the fluid to the desired level, enclosing the bag in which it is contained in the thermally insulating jacket, and maintaining it within the jacket during the period of fluid administration, the desired result of maintaining the patient body temperature at optimum levels may be obtained.

THE DRAWINGS

In the drawings:

FIGS. 1 and 2 are outside and inside elevations, respectively, of the herein described suspendable, thermally insulating jacket for I.V. fluid bags, with the jacket in its open condition and, in FIG. 2, with the I.V. fluid bag which the jacket is adapted to contain being indicated in dashed outline.

FIG. 3 is a view in elevation, similar to FIGS. 1 and 2, but illustrating the first stage of enclosure of the I.V. fluid bag by the jacket, and FIGS. 4 and 5 are front and back views, respectively, of the assembly of I.V. fluid bag and jacket in operative condition, with the jacket completely enclosing the I.V. fluid bag, ready for suspension on the I.V. pole or other support.

DESCRIPTION OF A PREFERRED EMBODIMENT OF THE INVENTION

The I.V. fluid bag with which the herein described suspendable, thermally insulating jacket cooperates comprises a clear plastic bag 10 having at its upper end a suspension loop 12 for suspending it from a cooperating hook and a connector or coupling 14 at its lower end for coupling it to the fluid discharge tube. The exterior of the bag is marked longitudinally with numerical indicia 16 indicating the fluid level within the bag.

The jacket which encloses the bag is indicated generally at 18. It is made of any suitable insulating material such as "Thinsulate" or "Thermoloft" encased in an outer covering of a durable, wear-resistant material such as "Taslanized" Nylon. The components of the jacket may be sewed together, or integrated by a combination of sewing and radio frequency welding.

The jacket is sufficiently large so that it may be wrapped around the I.V. fluid bag with its end segments in lapped relation. It thus is divided into segments which, for convenience of reference, are termed herein the back segment 20, the underlapped segment 22 and the overlapped segment 24.

Fastening means are provided for releasably fastening together the meeting surfaces of the jacket segments in their lapped condition. Burr-type "Velcro" fasteners are preferred for this purpose.

Accordingly three pairs of such fasteners 26–26a, 28–28a and 30–30a are positioned along the longitudinal margins of the jacket for maintaining them releasably in lapped condition.

Another pair 32-32a are positioned at the top of the jacket for maintaining the top in releasably closed condition.

Support means are provided for supporting the filled I.V. fluid bag within the jacket.

To this end, a support ring 34 is attached to the upper inner surface of central segment 20. It is designed for connection with an integral hook 36 with which the I.V. fluid bag may be provided.

Alternative or supplemental gravitational support means for the I.V. fluid bag comprise a pair of straps 38. These are arranged in laterally spaced apart position to accommodate the discharge connector between them. They are maintained in releasable closed position, preferably by means of burr-type fastener pairs 40, 40a and 42-42a.

The assembly of I.V. fluid bag and enclosing jacket is supported from the I.V. pole or other support by means of a loop 44 secured to the upper portion of central segment 20.

A window 46 is located in the jacket in a position such that it will register with numerical indicia 16 on the I.V. fluid bag. In the illustrated form of the invention, the window is located centrally of overlap segment 24, longitudinally thereof.

As a further feature, the external surface of jacket central segment 20 may mount one or more clear plastic pockets 48. These are adapted to contain data cards bearing such information such as the identification of the fluid contained in the fluid bag, the use to which it is to be put, etc.

Operation

In use, the jacket is hung in its open position by loop 44 from the I.V. pole or other support. The selected bag of I.V. fluid is hung by bag hook 36 on jacket ring 34. The jacket is closed around the bag, with burr-type fasteners 26-26a, 28-28a, 30-30a and 32-32a pressed together along the side, and top margins. Bag support straps are secured in position by fasteners 40-40a and 42-42a.

Fluid then may be withdrawn from the bag in the usual manner, noting the fluid level within the bag at any time through window 46.

If desired, the jacketed bag may be stored in a warming device until needed.

Comparative tests carried out with and without use of the herein described insulating jacket have indicated its efficiency in maintaining the fluid contents of the bag at the desired temperature. In carrying out these tests a Mon-a-therm Model 6500 temperature monitor was connected to a LaBarge Mon-a-therm tympanic temperature sensor. The cotton tip, umbrella retainer, and protective plastic tube were carefully removed from the temperature probe. The probe was inserted one inch into a 1000 ml Abbott Laboratories I.V. fluid bag. This was inserted through the lower front portion of the fluid bag through a 14 gauge Abbocath I.V. catheter sheath.

The tests indicated that a one liter bag of I.V. fluid warmed to 108° F. normally will lose 16-17° F. in one hour in a 68° F. atmosphere. This same bag of fluid will lose only 5° F. to 6.3° F. when wrapped in the thermal jacket of our invention.

A one liter bag of I.V. fluid warmed to 103.1° F. and placed in a 42° F. atmosphere will lose 31° F. in 60 minutes and 44.8° F. in 120 minutes. When wrapped in the herein described insulating jacket it will lose only 10.4° F. in 60 minutes and 18.4° F. in 120 minutes. The jacket thus is highly efficient in assisting emergency medical, operating room, and critical care personnel in the difficult task of keeping patients warm.

Having thus described in detail a preferred embodiment of the present invention, it will be apparent to those skilled in the art that various physical changes could be made without altering the inventive concepts and principles embodied. The present embodiment is therefore to be considered in all respects as illustrative and not restrictive, the scope of the invention being indicated by the appended claims. All changes which come within the meaning and range of equivalency of the claims are therefore to be embraced therein.

I claim:

1. In combination, an I.V. fluid bag having a discharge outlet in its lower end and a thermally insulating jacket therefor, the jacket comprising:
    (a) a sheet of thermally insulating material dimensioned to wrap around the bag with the ends of the sheet overlapped,
    (b) burr-type fastening means positioned on the jacket for releasably fastening together the overlapped ends of the sheet in the wrapped-around, bag-enclosing condition of the sheet,
    (c) bag support mean on the jacket for supporting the bag in the bag-enclosing condition of the sheet,
    (d) jacket support means on the jacket for supporting the jacket on an I.V. pole or other support, and
    (e) burr-type fastening means positioned at the bottom of the jacket in spaced apart relation for releasably closing the bottom of the jacket to form a gravitational support for the I.V. fluid bag while at the same time providing an opening dimensioned to accommodate the discharge outlet thereof.

2. In combination, an I.V. fluid bag having a discharge outlet in its lower end and marked longitudinally with calibration indicia, and a thermally insulating jacket therefor, the jacket comprising:
    (a) a sheet of thermally insulating material dimensioned to wrap around the bag,
    (b) fastening means positioned on the jacket for releasably fastening it in the wrapped-around, bag-enclosing condition of the sheet,
    (c) bag support means on the jacket for supporting the bag in the bag-enclosing condition of the sheet,
    (d) jacket support means on the jacket for supporting the jacket on an I.V. pole or other support, and
    (e) a longitudinal window on the jacket located opposite the calibration indicia for viewing the same.

* * * * *